United States Patent [19]

Ostapchenko

[11] Patent Number: 5,192,308

[45] Date of Patent: Mar. 9, 1993

[54] VASCULAR PROSTHESIS WITH AN ELASTOMER COATING

[75] Inventor: George J. Ostapchenko, Wilmington, Del.

[73] Assignee: E. I. Du Pont de Nemours and Company, Wilmington, Del.

[21] Appl. No.: 687,673

[22] Filed: Apr. 19, 1991

[51] Int. Cl.$^5$ .............................................. A61F 2/06
[52] U.S. Cl. ........................................ 623/1; 623/901; 427/2; 427/230; 427/235; 427/322
[58] Field of Search ................... 427/322, 307, 2, 235, 427/230, 245; 623/3, 901, 1

[56] References Cited

U.S. PATENT DOCUMENTS

| | | | |
|---|---|---|---|
| 2,838,799 | 6/1958 | Meister | 427/235 |
| 3,066,720 | 12/1962 | Fontaine | 118/408 |
| 3,524,755 | 8/1970 | Hochberg | 427/245 |
| 3,912,834 | 10/1975 | Imai et al. | 427/322 |
| 3,931,437 | 1/1976 | Civardi et al. | 427/322 |
| 4,460,747 | 7/1984 | Horak et al. | 427/307 |
| 4,634,447 | 1/1987 | Isono et al. | 427/235 |
| 4,784,880 | 11/1988 | Coplan et al. | 427/230 |
| 4,840,819 | 6/1989 | Williams et al. | 427/245 |

Primary Examiner—Shrive Beck
Assistant Examiner—Diana Dudash
Attorney, Agent, or Firm—Paul R. Steyermark

[57] ABSTRACT

A vascular prosthesis is made by wetting a porous polyester fiber tubing with water until it gains close to maximum amount of weight, removing excess liquid from inside the tubing, repeatedly contacting the inside surface of the tubing with a solution of a biocompatible polymer in a water-immiscible solvent to adsorb some solution on the inside surface of the tubing, and removing excess solution, then removing solvent from the adsorbed solution to form a nonporous elastomer coating of the desired thickness on the inside surface of the tubing.

10 Claims, No Drawings

VASCULAR PROSTHESIS WITH AN ELASTOMER COATING

BACKGROUND OF THE INVENTION

This invention relates to a vascular prosthesis with an elastomer coating that is mechanically strong, flexible, and substantially nonporous, and does not require preclotting prior to its implantation.

Vascular prostheses are used as substitutes for portions of blood vessels when portions of blood vessels in a patient must be removed or bypassed because of clotting or disease. Such prostheses can be made of synthetic materials, especially of woven or knit polyester tubing. This type of tubing is preferred to solid, extruded tubing because it is not as rigid or subject to kinking and, therefore, can be formed into a variety of shapes without difficulty and without unduly restricting the blood flow. Such porous tubing normally is soaked in the patient's blood, and the blood is allowed to clot prior to use. This makes the tubing nonporous and, in addition, it facilitates the growth of endothelial cells on the blood-coated surfaces. As an alternative, the woven or knit tubing is coated either on the inner or on the outer surface, or on both surfaces with a polymeric material, which makes the tubing nonporous. Some polymeric coatings also support endothelial cell growth. Such coated tubing eliminates the need for presoaking in patient's blood and preclotting.

Various methods of applying polymeric materials to porous tubing to form either porous or nonporous coatings for the purpose of making vascular prostheses are known. For example, U.S. Pat. No. 4,304,010 (to Mano) describes a porous poly(tetrafluoroethylene) vascular prosthesis tubing coated on the outside with elastomer materials, especially with fluorine rubbers. Coating can be applied from a solution also containing a blowing agent, or from a solution in a mixture of a solvent and a nonsolvent and drying to form a porous coating, or coating an elastomer solution on the outside of the tubing and removing the solvent by dipping the coated tubing in a nonsolvent bath and heating above the boiling point of the solvent to render the coating porous. U.S. Pat. No. 4,632,842 (to Karwoski et al.) describes a process for applying a fluorine-containing coating to a porous tubular substrate by means of a glow discharge. U.S. Pat. No. 4,656,083 (to Hoffman et al.) describes a process for treating articles to improve their biocompatibility by exposing a substrate material to plasma gas discharge in an inert gas atmosphere and then in the presence of an organic gas such as, for example, a halohydrocarbon.

As can be seen, the above processes either produce a porous coating, which is not intended here, or require rather complicated techniques and apparatus. It is, therefore, desirable to provide a substantially nonporous vascular prosthesis of a simple design, which can be made by a convenient and inexpensive process not requiring complicated special equipment.

SUMMARY OF THE INVENTION

According to the present invention, there is now provided a process for making a vascular prosthesis, said process comprising the following sequential steps:

(a) wetting with water a porous tubing made of polyester fibers for a sufficient time to cause the tubing to pick up water in an amount close to its maximum weight;

(b) removing excess water from the inside surface of the tubing, while still leaving water droplets in the interstices between the fibers forming the tubing;

(c) briefly contacting the inside surface of the tubing with a solution of suitable biocompatible elastomer in a solvent or combination of two or more solvents which are not miscible with water and removing excess of that solution beyond what remains adsorbed on the inside surface of the tubing;

(d) removing solvent from the thus adsorbed solution to form an elastomer coating on the inside surface of the tubing, and determining elastomer add-on; and (e) repeating steps (c) and (d) to the extent required to obtain sufficient add-on of elastomer to form a substantially continuous, nonporous elastomer coating on the inside surface of the tubing.

There also is provided a vascular prosthesis made by the above process.

DETAILED DESCRIPTION OF THE INVENTION

The preferred polyester fiber used in the preparation of the tubing used as the substrate in the process of the present invention is poly(ethylene terephthalate), sometimes abbreviated herein to PET. Experimental tubing of this type is available from various sources, but the use of such woven or knit tubing for vascular prostheses has already been suggested earlier and is not considered novel.

The term "biocompatible", as used herein, means relatively nonthrombogenic when used in direct contact with blood, as well as compatible with tissue. The biocompatibility of candidate elastomers can be determined by standard procedures well known to those skilled in the art.

The biocompatible elastomer can be of various types, although the preferred types are certain copolyetheresters. In particular, an outstanding copolyetherester elastomer for this purpose consists essentially of a multiplicity of recurring intralinear long chain and short chain ester units connected head-to-tail through ester linkages, such long chain ester units being represented by the following formula (I)

and short chain units being represented by the following formula (II):

where G is a divalent radical remaining after the removal of terminal hydroxyl groups from a poly(alkylene oxide) glycol having an average molecular weight above about 400 and a ratio of the number of alkylene oxide carbon to oxygen atoms of 2.5 to 4.3, preferably 2.5 to 3.5, and a melting point below about 60° C.;

D is a divalent radical remaining after the removal of hydroxyl groups from a diol having a molecular weight of less than about 250; and R and R' are divalent radicals remaining after the removal of carboxyl groups from a dicarboxylic acid having a molecular weight of less than 300;

with the proviso that
(a) the copolyetherester contains about 23–82 weight percent, preferably 23–35 weight percent of repeating units (II);
(b) at least about 80 percent of the combined R and R' groups (R+R') are 1,4-phenylene groups; and
(c) at least 80% of D groups in formula (II) are 1,4-butylene groups, also occasionally referred to herein as tetramethylene groups;

with the further proviso that the total percentage of (R+R') groups which are not 1,4-phenylene groups and of D groups which are not 1,4-butylene groups is at most 20%.

The polymeric glycols from which the long chain group G is derived preferably have a molecular weight of about 400–4000. Representative polymeric glycols of this type include poly(1,2- and 1,3-propylene oxide) glycol, poly(tetramethylene ether) glycol, random or block copolymers of ethylene oxide with 1,2-propylene oxide, and random copolymers of tetrahydrofuran with minor amounts of a second monomer such as, for example, 3-methyltetrahydrofuran.

Low molecular weight diols from which the short chain group D is derived include, among others, 1,4-butanediol, 1,3-propanediol, ethylene glycol, and cyclohexanedimethanol.

When the proportion of short chains in the copolyetherester is within the 23–35 weight percent range, the balance of the copolyetherester's properties, including tear strength, solvent resistance, and elastomeric properties is the best.

Copolyetheresters containing long chains derived from a polymeric glycol containing 80–97 mole percent of copolymerized tetrahydrofuran and 3–20 mole percent of a copolymerized cyclic alkylene oxide containing 2, 3, or 4 carbon atoms and poly(tetramethylene terephthalate) short chains are described in U.S. Pat. No. 4,906,729 to Greene et al., which is incorporated by reference herein.

The preferred copolyetheresters can be made by conventional ester interchange from dimethyl terephthalate, 1,4-butanediol, and poly(tetramethylene ether) glycol having a molecular weight of about 600–2000.

Other suitable biocompatible elastomers will be those that are soluble in the particular water-immiscible solvent used in step (c) of the process. Elastomer solubility in a given solvent can be established by a simple experiment. Further, if a single water-immiscible solvent does not dissolve a biocompatible elastomer sufficiently well, a mixture of two or more such solvents can be used. Because there are many possible elastomers, including, for example, spandex type polyurethanes and others, and many possible solvents and solvent combinations that would be operable with such elastomers, specific elastomers and solvents or their combinations will not be listed here. One skilled in the art would first select an elastomer and establish that it is biocompatible and then would select the best water-immiscible solvent or solvent combination. The present invention states a principle which is readily applicable across the board and is not limited to the elastomers or solvents recited in the specification or illustrated in the example.

All the copolyetheresters of the type described above are well known and some are commercially available. For example, satisfactory copolyetherester elastomers are offered by E. I. du Pont de Nemours and Company under the trademark HYTREL ®.

Suitable PET fibers for knitting or weaving the vascular prosthesis substrate are available from several sources, including E. I. du Pont de Nemours and Company, which offers the fibers under the trademark DACRON ®. The usual fineness of the fibers is about 75 to 300 deniers, as this term is understood in the industry; this corresponds to 8.33 to 33.33 g/km.

In the practical operation of the process of the present invention, a knit or woven PET tubing of suitable inside diameter, usually at least 4 mm, and suitable length, usually several cm, is soaked in water or otherwise contacted with water at room temperature for a period such that it can no longer absorb water, as determined by repeated weighings. Depending on the tightness of the weave or knitting of the polyester tubing, weight increase may be as small as 25% or as large as 200% or even larger. Excess water can be removed from the inside of the tubing in any convenient manner, for example, by placing the tubing in the vertical position and tapping it gently against a hard surface but preferably is blown out with compressed air or compressed nitrogen. The tubing is not allowed to dry but is promptly placed in a substantially vertical position to facilitate a uniform coating thickness in the circumferential direction, and a solution of elastomer in an appropriate solvent is poured through the inside of the tubing. Obviously, other techniques for introducing the solution into the tubing may be equally satsfactory; for example, aspiring the solution into the tubing by means of reduced pressure.

Suitable solvents must be immiscible with water. In addition, one must select a solvent or solvent combination that is, under the conditions of this process, inert to the polyester material of the tubing, so that the polyester fibers would not themselves be dissolved or weakened. Copolyetheresters are soluble in chlorinated solvents such as, for example, methylene chloride, carbon tetrachloride, and perchloroethylene. Preferably, the solvent has a low boiling temperature, so that it can be readily removed at room or slightly above room temperature.

After the elastomer solution is passed through the tubing, solvent can be conveniently evaporated from the inside of the tubing, for example, by blowing nitrogen therethrough or by subjecting the tubing to reduced pressure. The tubing is then dried, preferably at a reduced pressure, at a moderate temperature, for example, 80° C. or less. The coated tubing is weighed to determine elastomer add-on, and from that figure the thickness of elastomer layer can be calculated. This coating procedure can be repeated as many times as necessary in order to obtain the desired thickness. Wetting with water is normally not required after the initial coating has been applied.

The procedure of this invention is very simple to practice and gives a product having excellent physical properties, which has very good flexibility and small kink radius. By contrast, soaking the woven or knit polyester tubing in elastomer solution or pouring elastomer solution into the tubing without prior saturation of the tubing with water would result in a stiffer product, which would have a much more pronounced tendency to kink. The absorption of water into the fibers prevents the fibers from absorbing the solution; and, because the solvent in which the elastomer is dissolved is immiscible with water, there is no penetration of the solution into the fibers and concomitant interchange of solution with water within the fibers.

This invention is now illustrated by the following representative example, which should not be considered as limiting. Other suitable elastomers or solvents and other specific operating steps may be employed, so long as the principal requirement of this invention is observed, namely, that the polyester tubing first be saturated with water, that excess water be removed from the inside of the tubing, and that a solution of elastomer in a solvent immiscible with water be introduced into the tubing and the solvent be removed. In the example, all parts, proportions, and percentages are by weight.

EXAMPLE

An experimental poly(ethylene terephthalate) vascular prosthesis in the form of a 10 cm long straight woven tubing having an inside diameter of 4 mm was wetted on the outside surface with distilled water, to produce a weight increase of about 100%. Excess water was blown away with nitrogen from the inside of the tubing, leaving water droplets in the interstices between the fibers forming the tubing. With the tubing placed in a vertical position, 2 ml of a 5% solution of copolyetherester in methylene chloride was allowed to flow through the tube. The copolyetherester was prepared in the known manner from the following starting materials:

| Compound | Parts |
|---|---|
| poly(tetramethylene ether glycol) Molecular weight, $M_n$, about 2100 | 725 |
| 1,4-butanediol | 94 |
| dimethyl terephthalate | 269 |
| trimethyl trimellitate | 0.53 |
| 1,3,5-trimethyl-2,4,6-tris-(3,5-di-tert-butyl-4-hydroxybenzyl)benzene | 5 |

The copolyetherester had an inherent viscosity in m-cresol at a concentration of 1 g/L at 30° C. of 1.65.

Dry nitrogen was next blown through the tubing to evaporate the solvent. The tubing was inverted and coated again in the same manner but omitting the initial wetting step. It was vacuum-dried at 80° C. for about 30 minutes. Visual inspection revealed a uniformly coated inner surface of the tubing, while no elastomer was seen on the outer surface. The thickness of the coating, calculated from the weight increase and the dimensions of the tubing, was 0.44 mm.

I claim:

1. A process for making a vascular prosthesis, said process comprising the following sequential steps:
   (i) wetting with water a porous tubing made of polyester fibers for a sufficient time to cause the tubing to pick up water in an amount close to the maximum absorbable weight thereof;
   (ii) removing excess water from the inside surface of the tubing, while still leaving water droplets in the interstices between the fibers forming the tubing;
   (iii) briefly contacting the inside surface of the tubing with a solution of a copolyetherester consisting essentially of a multiplicity of recurring intralinear long chain and short chain ester units connected head-to-tail through ester linkages, such long chain ester units being represented by the following formula (I):

  (I)

and short chain units being represented by the following formula (II):

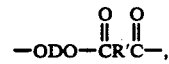  (II)

where G is a divalent radical remaining after the removal of terminal hydroxyl groups from a poly(alkylene oxide) glycol having an average molecular weight above about 400 and a ratio of the number of alkylene oxide carbon to oxygen atoms of 2.5 to 4.3, preferably 2.5 to 3.5, and a melting point below about 60° C.;

D is a divalent radical remaining after the removal of hydroxyl groups from a diol having a molecular weight of less than about 250; and R and R' are divalent radicals remaining after the removal of carboxyl groups from a dicarboxylic acid having a molecular weight of less than 300;

with the proviso that
(a) the copolyetherester contains about 23–82 weight percent of repeating units (II);
(b) at least about 80 percent of the combined R and R' groups R+R') are 1,4-phenylene groups; and
(c) at least 80% of D groups in formula (II) are 1,4-butylene groups;

with the further proviso that the total percentage of (R+R') groups which are not 1,4-phenylene groups and of D groups which are not 1,4-butylene groups is at most 20%; in a solvent or combination of two or more solvents which are not miscible with water and removing excess of that solution beyond what remains absorbed on the inside surface of the tubing;

(iv) removing solvent from the thus adsorbed solution to form an elastomer coating on the inside surface of the tubing, and determining elastomer add-on; and (v) repeating steps (iii) and (iv) to the extent required to obtain sufficient add-on of elastomer to form a substantially continuous, nonporous coating on the inside surface of the tubing.

2. The process of claim 1 wherein the copolyetherester contains 25–35 weight percent of repeating units (II).

3. The process of claim 1 wherein at least one solvent is a halogenated hydrocarbon selected from the group consisting of methylene chloride, carbon tetrachloride, and perchloroethylene.

4. The process of claim 3 wherein only one solvent is employed.

5. The process of claim 4 wherein the solvent is methylene chloride.

6. The process of claim 1 wherein polyester is poly(ethylene terephthalate).

7. A vascular prosthesis made by the process of claim 1.

8. A vascular prothesis made by the process of claim 6.

9. A vascular prothesis of claim 7 which has an inside diameter of at least 4 mm.

10. A vascular prothesis of claim 8 which has an inside diameter of at least 4 mm.

* * * * *

UNITED STATES PATENT AND TRADEMARK OFFICE
CERTIFICATE OF CORRECTION

PATENT NO. : 5,192,308

DATED : March 9, 1993

INVENTOR(S) : GEORGE JOSEPH OSTAPCHENKO

It is certified that error appears in the above-identified patent and that said Letters Patent is hereby corrected as shown below:

Col. 6, claim 1, line 29, insert --(-- before R + R').

Signed and Sealed this

Eighth Day of February, 1994

BRUCE LEHMAN

*Attest:*

*Attesting Officer*     *Commissioner of Patents and Trademarks*